United States Patent [19]

Strom

[11] 4,410,736

[45] Oct. 18, 1983

[54] COUPLING OF PHENOLS WITH DIPHENOQUINONES

[75] Inventor: Robert M. Strom, Midland, Mich.

[73] Assignee: The Dow Chemical Company, Midland, Mich.

[21] Appl. No.: 251,627

[22] Filed: Apr. 6, 1981

[51] Int. Cl.$^3$ .............................................. C07C 39/15
[52] U.S. Cl. ..................................... 568/730; 568/722
[58] Field of Search ........................ 568/730, 722, 723

[56] References Cited

U.S. PATENT DOCUMENTS 3,562,338  2/1971  Zaweski ............................. 568/730
3,631,208  12/1971  Hay .................................... 568/730
3,804,865  4/1974  Rutledge ............................ 568/730
4,098,830  7/1978  Rutledge ............................ 568/730
4,238,627  12/1980  Reichle .............................. 568/730

Primary Examiner—Werren B. Lone
Attorney, Agent, or Firm—Douglas N. Deline

[57] ABSTRACT

Substituted biphenols are produced by the oxidative coupling of phenolic reactants in the presence of a heterogeneous oxidative coupling catalyst and thereafter further contacting the reaction product with additional phenolic reactant in the presence of a heterogeneous reduction catalyst in the substantial absence of oxygen.

6 Claims, No Drawings

COUPLING OF PHENOLS WITH DIPHENOQUINONES

BACKGROUND OF THE INVENTION

This invention relates to a process for making substituted biphenols. In particular, this invention relates to a process for making substituted biphenols by reacting phenols with diphenoquinones.

Biphenols are useful as bactericides, chemical intermediates, copolymers, and especially as antioxidants. For example, 2,2',6,6'-tetra-t-butyl-p,p'-biphenol is an excellent antioxidant in a broad range of organic materials. It can be used to stabilize such materials as animal and vegetable fats or oils, gasoline, lubricants, polyolefins such as polyethylene and polypropylene, and both natural and synthetic rubber. It exerts its protective effect by merely incorporating it uniformly throughout the organic material in small amounts. Concentrations of from about 0.1 to 1 weight percent usually provide adequate antioxidant protection. When the substituted p,p'-biphenol compound contains easily removable alkyl substituents such as tertiary alkyl, the compound may also be easily dealkylated to form p,p'-biphenol, a useful monomer in polyester production.

In U.S. Pat. No. 3,562,338, a process for preparing these compounds is disclosed in which 3,3',5,5'-tetrahydrocarbyl diphenoquinones are first prepared by an oxidative coupling reaction of a 2,6-dihydrocarbyl phenol in the presence of an alkali metal hydroxide. The 3,3',5,5'-tetrahydrocarbyl diphenoquinone is then allowed to react with extra 2,6-dihydrocarbyl phenol to form the desired product 2,2',6,6'-tetrahydrocarbyl-p,p'-biphenol.

Similarly, in U.S. Pat. No. 3,631,208 substituted biphenols were prepared by reaction of phenols with diphenoquinones in the presence of acidic or basic catalysts such as carboxylic acids, amines or metal hydrocarbon oxides.

Because prior art processes employed acidic or basic catalysts a separate neutralization step was required to neutralize the catalyst which results in contamination of products with salt by-products.

SUMMARY OF THE INVENTION

This invention comprises an improved process for making substituted biphenol compounds comprising reacting by contacting a substituted phenol or mixture thereof having the formula:

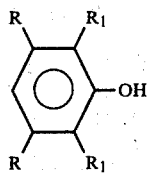

wherein each R is either hydrogen, halogen, or $R_1$; and each $R_1$ is a substituent having up to 10 carbons selected from hydrocarbon, halohydrocarbon or hydrocarbonoxy, with a substituted diphenoquinone of the formula

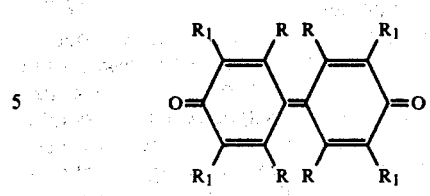

where R and $R_1$ are previously defined in a liquid reaction medium comprising a lower alkanol and recovering the substituted biphenol reaction product.

The improved process of the instant invention provides for the expeditious recovery of the substituted biphenol product inasmuch as the lower alkanol can be removed by distillation. Thus no neutralization of acidic or basic catalyst is required according to the invention and the product may be easily recovered without contamination with catalysts or by-products thereof.

DETAILED DESCRIPTION OF THE INVENTION

The substituted phenol reactants here used are those well-known in the art as forming oxidative carbon-carbon coupling products. Examples are 2,3,6-trimethyl phenol, 2,6-diethyl phenol, 2,6-ditertiary butyl phenol, 2,6-diisopropylphenol, 6-t-butyl-o-cresol, 2,6-di-sec-butylphenol, 2,6-di(2,4,4-trimethyl-2-pentyl)phenol, 2-butyl-6-cyclohexylphenol, 6-cyclohexyl-o-cresol, 6-(α-methylbenzyl)-o-cresol, 2,6-di(α-methylbenzyl)phenol, 6(α,α-dimethylbenzyl)-o-cresol, 2-sec-butyl-6-(α-methylbenzyl)phenol, 6-phenyl-o-cresol, 2-(3,5-di-t-butylphenyl)-6-t-butylphenol, and 6-isopropyl-o-cresol, 2,6-dimethoxy phenol, 2,6-dibutoxy phenol, 3-chloro-2,6-dimethyl phenol, 2-ethoxy-3,6-dimethyl phenol, 3,5-dichloro-2,6-ditertiary butyl phenol, etc.

Preferred phenol reactants are 2,6-disubstituted phenols. The most preferred phenols are 2,6-dialkyl phenols, especially those wherein the alkyl group is easily removable from the biphenol product such as tertiary alkyl.

As is known to the skilled artisan, the substituted phenols of formula I are readily coupled by a variety of methods to form diphenoquinones of formula II. Any suitable method for forming the diphenoquinone may be employed according to the instant invention. A preferred process involves the oxidative coupling of the substituted phenol by contacting the phenol with a heterogeneous oxidative coupling catalyst in the presence of an oxygen-containing gas. A particularly preferred process further involves conducting such oxidative coupling reaction in the presence of a liquid reaction medium comprising methanol which has been found to unexpectedly promote the oxidative coupling reaction. Therefore, claimed as one embodiment of the present invention is the process wherein a substituted phenol is contacted with an oxygen-containing gas in the presence of a heterogeneous oxidative coupling catalyst in a liquid reaction medium comprising methanol followed by the further reduction of such diphenoquinone so formed by contacting with a phenol of formula I in the presence of a liquid reaction medium comprising a lower alkanol. In this manner not only may high conversions of phenol reactant be obtained in short reaction times, but no contamination by acidic or basic catalysts or the by-products thereof results. The desired substituted p,p'-biphenol reaction product is easily recovered in high yield and purity according to a greatly simplified process.

Further preferred is the use in the oxidative coupling reaction of a liquid reaction medium comprising orthodichlorobenzene, the resulting diphenoquinone produced by such process has unexpectedly been found to be particularly reactive with further phenolic reactants in the process of the present invention. While not wishing to be bound by any particular theory of operation, the enhanced reactivity of the diphenoquinone so produced is believed to be due to a small but catalytically effective amount of hydrochloric acid or other species coproduced in the reaction medium when orthodichlorobenzene is present.

According to the preferred process the heterogeneous oxidative coupling catalysts employed comprise metals of groups VIII or IB of the Periodic Table along with chromium, molybdenum, zinc or mixtures thereof present in a valence suitable for catalyzing the carbon-carbon coupling of phenolic compounds of formula I. Most usually the catalysts are present as the corresponding metal oxide. Preferred catalysts are the noble metals present in a suitable valence, as previously explained. Most preferred are noble metal oxides, e.g., the oxides of platinum, palladium, ruthenium, rhodium, iridium and osmium. Especially preferred are the oxides of platinum and palladium.

The catalyst may be and preferably is present in a highly dispersed form, having large surface area. Thus, finely commutated or powdered catalysts or supported catalysts in which the catalyst is deposited onto a large surface area, supporting means such as carbon black, bone black, activated charcoal, alumina, etc. are suitable.

It is additionally sometimes desirable in order to inhibit the isomerization of 2,6-dihydrocarbyl phenol, that the reaction mixture be neutralized. For example, the effect of acidic species introduced by means of impurities in the catalyst or by means of the catalyst support may be counteracted by addition to the reaction mixture of an effective amount of a basic species such as an alkali metal carbonate or an alkali metal hydroxide.

The oxidative coupling reaction is conducted at a temperature sufficient to obtain a reasonable reaction rate. The higher the temperature, the faster the rate. Generally, good oxidation results are obtained at a temperature of from about 30° C. to 300° C. A preferred temperature range during the oxidation stage of the reaction is from 50° C. to 100° C.

Oxidation of the substituted phenol is accomplished by passing an oxygen-containing gas through the reaction mass. Although other oxygen-containing gases or even oxygen itself can be used, the preferred oxidant is air.

The oxidation can be conducted at atmospheric pressure or at higher pressures. Preferably, the oxidation is conducted under moderate pressures because this results in a faster reaction. A preferred pressure range is from atmospheric to about 1000 psig. A most useful range is from about 200 to 500 psig.

It is understood that any suitable means of producing the substituted diphenoquinone may be employed according to the instant invention, including such additional processes as are taught, for example, in U.S. Pat. Nos. 3,552,052; 3,804,865; 4,086,253; etc., which teachings are incorporated herein by reference.

In the operation of the invention the diphenoquinone of formula II produced by any suitable means is contacted with one or more phenols of formula I in a liquid reaction medium comprising a lower alkanol. Preferably the lower alkanol has a boiling point less than about 150° C. so that it may be easily stripped from the reaction product at moderate temperatures less than the decomposition temperature of the products and less than the boiling point of possible contaminating liquid reactants such as the phenolic compound of formula I. Most preferably, the lower alkanol is methanol.

The liquid reaction medium may consist essentially of the lower alkanol or contain other liquid compounds in addition to the lower alkanol. For example, it has been previously mentioned that t-butyl-substituted biphenol compounds may be easily dealkylated to produce p,p'-biphenol. This dealkylation is advantageously conducted in a non-polar, preferably aromatic, solvent system wherein the alkylated compound is soluble but the dealkylated p,p'-biphenol compound is insoluble. Particularly suitable solvent systems for the dealkylation reaction include diethylbenzenes, dichlorobenzenes and other high boiling aromatic compounds. Therefore, in a complete process involving the formation of t-butyl-substituted diphenoquinones of formula II, then reaction with t-butyl-substituted -phenols of formula I and the subsequent dealkylation of the p,p'-biphenol product, an especially preferred liquid reaction medium comprises a mixture of methanol and an aromatic compound, preferably diethylbenzenes or dichlorobenzenes. The presence of methanol greatly aids in the oxidative coupling and reduction steps and the presence of the aromatic liquid is advantageous for the dealkylation reaction. The methanol may be easily removed from the reaction mixture by distillation prior to the dealkylation process.

The reaction between the phenol and the diphenoquinone occurs readily in the presence of the aforementioned lower alkanol. In practice, the diphenoquinone of formula II is merely contacted with a phenol of formula I in the presence of the lower alkanol and optionally other components of the liquid reaction medium and any remaining catalyst or other components which may be in the mixture as a result of the oxidative coupling reaction. That is, it is not required to filter or otherwise purify the diphenoquinone reactant mixture prior to reaction with the phenol according to the instant invention.

The reaction may be conducted without use of an inert atmosphere. However, use of additional amounts of air or oxygen is not desired. The reaction proceeds at a suitable rate without employing elevated pressures although such may be used if desired.

The diphenoquinone of formula II and the phenol of formula I are contacted in about a stoichiometric molar ratio. In practice, molar ratios of diphenoquinone to phenol from about 1:1 to about 1:4 may be employed. Preferred is a ratio of about 1:2.

The reaction is conducted at elevated temperatures. Generally, the higher the temperature the faster the reaction rate. However, extremely high temperatures may lead to degradation of product. Suitably, temperatures from about 50° C. to about 350° C. may be employed. Preferred are temperatures from about 60° C. to about 150° C.

The reaction is continued until the yield of the desired substituted biphenol compound is at a maximum. Generally, reaction from about 1 to about 4 hours is sufficient.

The product may be recovered if desired, for example, by merely allowing the reaction mixture to crystalize. As previously explained, if the dealkylated product is desired it is not necessary to recover the substituted biphenol reaction product. Instead the reaction mass is merely subjected to dealkylation conditions thereby producing p,p'-biphenol in high yield. With the proper choice of liquid reaction medium, the p,p'-biphenol readily precipitates and is easily recovered from the reaction medium.

The following examples illustrate the previously described invention.

EXAMPLE 1

2,6-Di-t-butylphenol (50 g) was charged to a 300-ml nickel pressure reactor equipped with mechanical stirrer and heating mantle. o-Dichlorobenzene (about 50 g) was added along with 2.5 g of a 5 percent palladium-on-carbon catalyst commercially available from Engelhard Minerals and Chemicals Corporation. Analysis of the catalyst surface by Electron Spectroscopy for Chemical Analysis (ESCA) indicated only palladium oxide was present.

The reactor was heated to about 100° C. with stirring under oxygen pressure (250 psig) for about 1 hour. The pressure was then vented and the product filtered while hot to separate catalyst. After solvent evaporation substantially pure 3,3',5,5'-tetra-t-butyl diphweoquinone was recovered.

EXAMPLE 2

Four grams of the 3,3',5,5'-tetra-t-butyl diphenoquinone produced in Example 1 were placed in a 50-ml round-bottom glass flask equipped with a reflux condensor and a mechanical stirrer. Five grams of di-t-butyl phenol, 25 ml of methanol and about 1 g of the previously disclosed 5 percent palladium-on-carbon catalyst were added. The mixture was then heated under nitrogen atmosphere to about 60° C.

After the following indicated time periods, the amount of 2,2',6,6'-tetra-t-butyl biphenol produced was determined by gas liquid chromatography. The weight ratio of 2,2',6,6'-tetra-t-butyl-p,p'-biphenol to 3,3',5,5'-tetra-t-butyl diphenoquinone in the product mixture is given in Table I.

TABLE I

| Time (hr) | Ratio (biphenol/diphenquinone) |
|---|---|
| 0 | 0/100 |
| 3 | 52/48 |
| 4 | 99/1 |

EXAMPLE 3

2,6-Di-t-butylphenol (25 g) was charged to a 300-ml stainless steel pressure reactor equipped with mechanical stirrer and heating mantle. o-Dichlorobenzene solvent (about 25 g) was added along with the previously described 5 percent palladium-on-carbon catalyst (1.25 g) and a small amount of sodium carbonate (0.25 g). The reactor was sealed and pressurized with oxygen to 250 psig then heated to 50° C. with stirring for a total of 50 minutes.

After 50 minutes, heating was discontinued and the reactor vented. The resulting mixture contained substantially pure 3,3',5,5'-tetra-t-butyl diphenoquinone as determined by gas liquid chromatography.

An additional quantity of 2,6-di-t-butylphenol (50 g) was added to provide a mole ratio of phenolic compound to diphenoquinone of about 4:1. The original heterogeneous oxidative coupling catalyst and sodium carbonate originally added to the reactor remained in the reaction mixture. The reactor was sealed and purged with nitrogen gas then heated to 80° C.–90° C. for the below indicated time periods. Analyses of samples from the reaction mixture were made by gas liquid chromatography and are contained in Table II.

TABLE II

| Time (hr) | Ratio (biphenol/diphenquinone) |
|---|---|
| 0 | 0/100 |
| 3 | 18/82 |
| 17 | 54/46 |

By comparison of the results of Table II with those of Table I it is seen that suitable rates of reaction between a phenolic and a diphenoquinone reactant may be obtained if a lower alkanol is employed as the liquid reaction medium and the acid or base catalyst is omitted. The advantage obtained by practice according to Example 2 is that no acid or base catalyst remains in the reaction mixture which must be neutralized and removed as has been the case in prior art processes.

What is claimed is:

1. In the process for making substituted biphenols by contacting a substituted phenol or mixture thereof of the formula

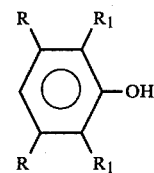

wherein each R is hydrogen, halogen or $R_1$; and each $R_1$ is a substituent having up to 10 carbons selected from the group consisting of hydrocarbon, halohydrocarbon and hydrocarbonoxy with a substituted diphenoquinone of the formula

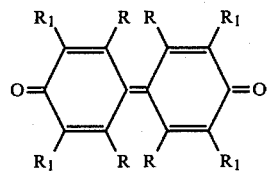

wherein R and $R_1$ are as previously defined in a liquid reaction medium, the improvement wherein the liquid reaction medium comprises a lower alkanol and the reaction is conducted in the substantial absence of base.

2. The process according to claim 1 wherein the lower alkanol has a normal boiling point less than about 100° C.

3. The process according to claim 1 wherein the lower alkanol is methanol.

4. A process for making substituted biphenols comprising
    (a) contacting a substituted phenol or mixture thereof of the formula

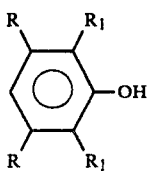 I wherein each R is hydrogen, halogen or $R_1$; and each $R_1$ is a substituent having up to 10 carbons selected from the group consisting of hydrogen, halohydrocarbon and hydrocarbonoxy, with an oxygen-containing gas in the presence of a heterogeneous oxidative coupling catalyst comprising a metal selected from the group consisting of the metals of groups VIII or IB of the Periodic Table, chromium, molybdenum, zinc and mixtures thereof present in a valence suitable for catalyzing the carbon-carbon coupling of the substituted phenol or mixtures thereof in the presence of a liquid reaction medium comprising methanol, for a time sufficient to produce substantial amounts of a substituted diphenoquinone of the formula

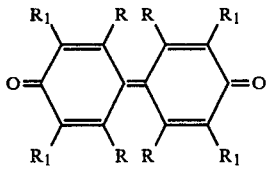 II wherein R and $R_1$ are as previously defined; and
(b) thereafter contacting the substituted diphenoquinone with a substituted phenol or mixture thereof of formula I in a liquid reaction medium comprising methanol in the substantial absence of base.

5. The process according to claim 4 wherein the heterogeneous oxidative coupling catalyst comprises a noble metal oxide.

6. The process according to claim 4 wherein in step (a), the liquid reaction medium further comprises o-dichlorobenzene.

* * * * *